United States Patent
Sakai et al.

[11] Patent Number: 5,229,435
[45] Date of Patent: Jul. 20, 1993

[54] SKIN-PROTECTING COMPOSITION

[75] Inventors: Yoshio Sakai, Takefu; Izumi Saitoh, Nishinomiya, both of Japan

[73] Assignees: Shionogi & Co., Ltd., Osaka; Nissin Chemical Industry Co., Ltd., Takefu, both of Japan

[21] Appl. No.: 502,772

[22] Filed: Apr. 2, 1990

[30] Foreign Application Priority Data

Apr. 1, 1989 [JP] Japan .................. 1-82547

[51] Int. Cl.$^5$ .................. C08L 33/08; C08L 83/07; C08F 30/08; C08F 230/08
[52] U.S. Cl. .................. 523/105; 526/279
[58] Field of Search .................. 523/105; 526/318.4, 526/279, 318.1, 318.2, 318.3

[56] References Cited

U.S. PATENT DOCUMENTS

| | | | |
|---|---|---|---|
| 2,716,638 | 8/1955 | Cohen et al. | 526/279 |
| 3,707,518 | 12/1972 | Bemmels et al. | 526/279 |
| 3,966,687 | 6/1976 | Ribba | 526/279 |
| 4,189,546 | 2/1980 | Deichert et al. | 526/279 |
| 4,242,483 | 12/1980 | Novicky | 526/279 |
| 4,478,990 | 10/1984 | Kohno et al. | 526/279 |
| 4,602,074 | 7/1986 | Mizutani et al. | 526/279 |
| 4,696,974 | 9/1987 | Sulc et al. | 523/105 |
| 4,874,830 | 10/1989 | Saitoh et al. | 526/318.4 |
| 4,914,140 | 4/1990 | Saitoh et al. | 523/105 |

*Primary Examiner*—Paul R. Michl
*Assistant Examiner*—Peter Szekely
*Attorney, Agent, or Firm*—Wenderoth, Lind & Ponack

[57] ABSTRACT

A skin-protecting composition which comprises a silicone-acrylic copolymer which comprises
(A) 1 to 15% by weight of a silicon-containing monomer,
(B) 30 to 70% by weight of an alkyl acrylate,
(C) 0 to 30% by weight of an alkyl methacrylate, and
(D) 5 to 45% by weight of a mono-ethylenically unsaturated monomer having a carboxyl group, and a medium, which can effectively block irritative materials and be easily removed from a skin.

10 Claims, 8 Drawing Sheets

SKIN-PROTECTING COMPOSITION

BACKGROUND OF THE INVENTION

1. Field of the Invention

The present invention relates to a skin-protecting composition. In particular, the present invention relates to a skin-protecting composition comprising an uncrosslinked silicone-acrylic copolymer which is soluble in a general solvent such as an alcohol and a weakly alkaline aqueous solution, a film formed from which copolymer has good skin-protecting properties.

2. Description of the Related Art

There are known skin-protecting agents which protect human skin from chemicals or other irritative materials.

The protecting agent is applied to the skin by coating or spraying to form a film which protects the skin. However, the conventional protecting agents have drawbacks such that an organic solvent in the agent such as acetone or ethyl acetate irritates the skin or the formed film is not easily removed from the skin.

U.S. Pat. No. 4,874,830 and Japanese Patent Kokai Publication No. 104909/1988 discloses a skin-protecting agent for protecting the skin of persons who wash dishes or apparatus with neutral detergents at home or in restaurants, hospitals, beauty shops and the like, which agent comprises an ethyl acrylate-methacrylic acid copolymer and ethylcellulose. The proposed skin-protecting agent effectively blocks many irritative materials, although some low molecular weight irritative materials permeate through the film of the agent.

SUMMARY OF THE INVENTION

An object of the present invention is to provide a skin-protecting composition not containing such an organic solvent as to stimulate the skin and effectively blocking irritative materials.

Another object of the present invention is to provide a skin-protecting composition which forms an easily removable film.

These and other objects are achieved by a skin-protecting composition which comprises a silicone-acrylic copolymer which comprises (A) 1 to 15% by weight of a silicon-containing monomer of the formula:

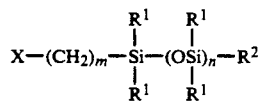

wherein X is a radically polymerizable group; $R^1$ groups are the same or different and each a $C_1$-$C_{20}$ hydrocarbon or halogenated hydrocarbon group or a group Y of the formula:

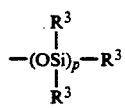

in which $R^3$ groups are the same or different and each a $C_1$-$C_{20}$ hydrocarbon or halogenated hydrocarbon group, p is a number of 5 to 100, provided that the number of the Y group among the $R^1$ groups is 0, 1 or 2; $R^2$ is a $C_1$-$C_{20}$ hydrocarbon or halogenated hydrocarbon group; m is a number of 1 to 10; and n is a number of 5 to 100, (B) 30 to 70% by weight of an alkyl acrylate,
(C) 0 to 30% by weight of an alkyl methacrylate, and
(D) 5 to 45% by weight of a mono-ethylenically unsaturated monomer having a carboxyl group, and a medium.

DETAILED DESCRIPTION OF THE INVENTION

Figure 1:
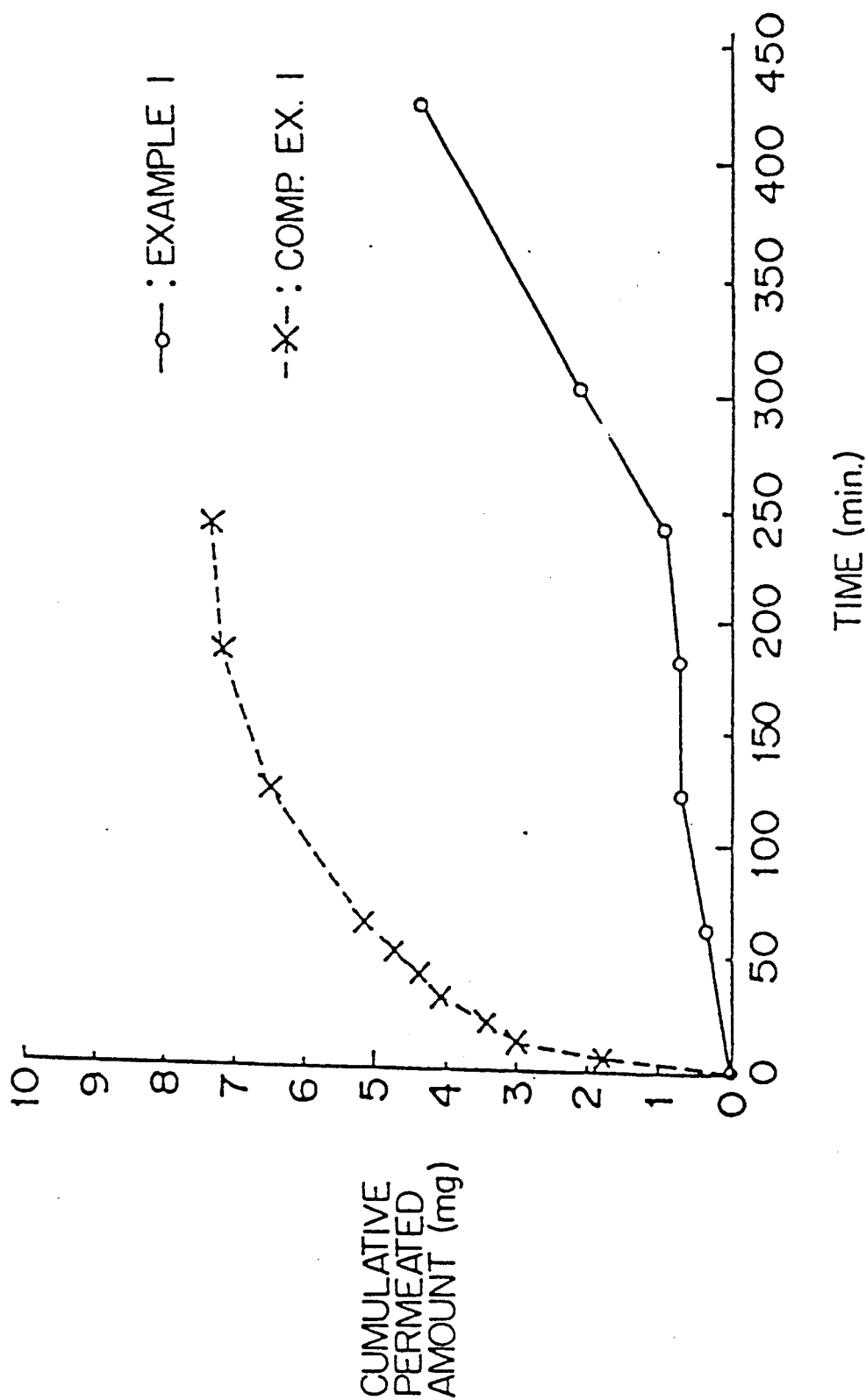
FIGS. 1 to 8 show the cumulative permeated amounts of the chemicals through the films formed from the copolymers of Examples and Comparative Examples.
Figure 2:
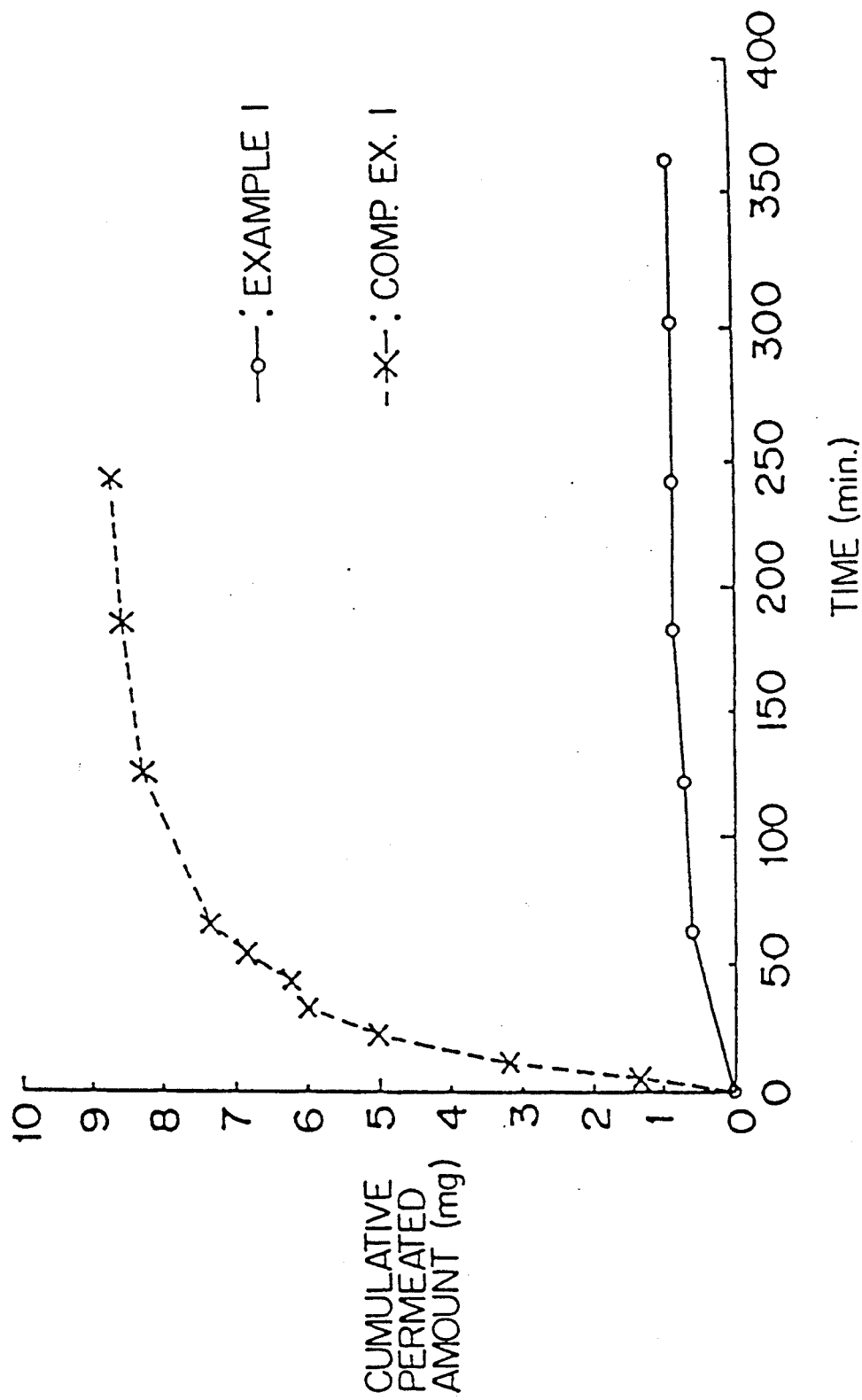
Figure 3:
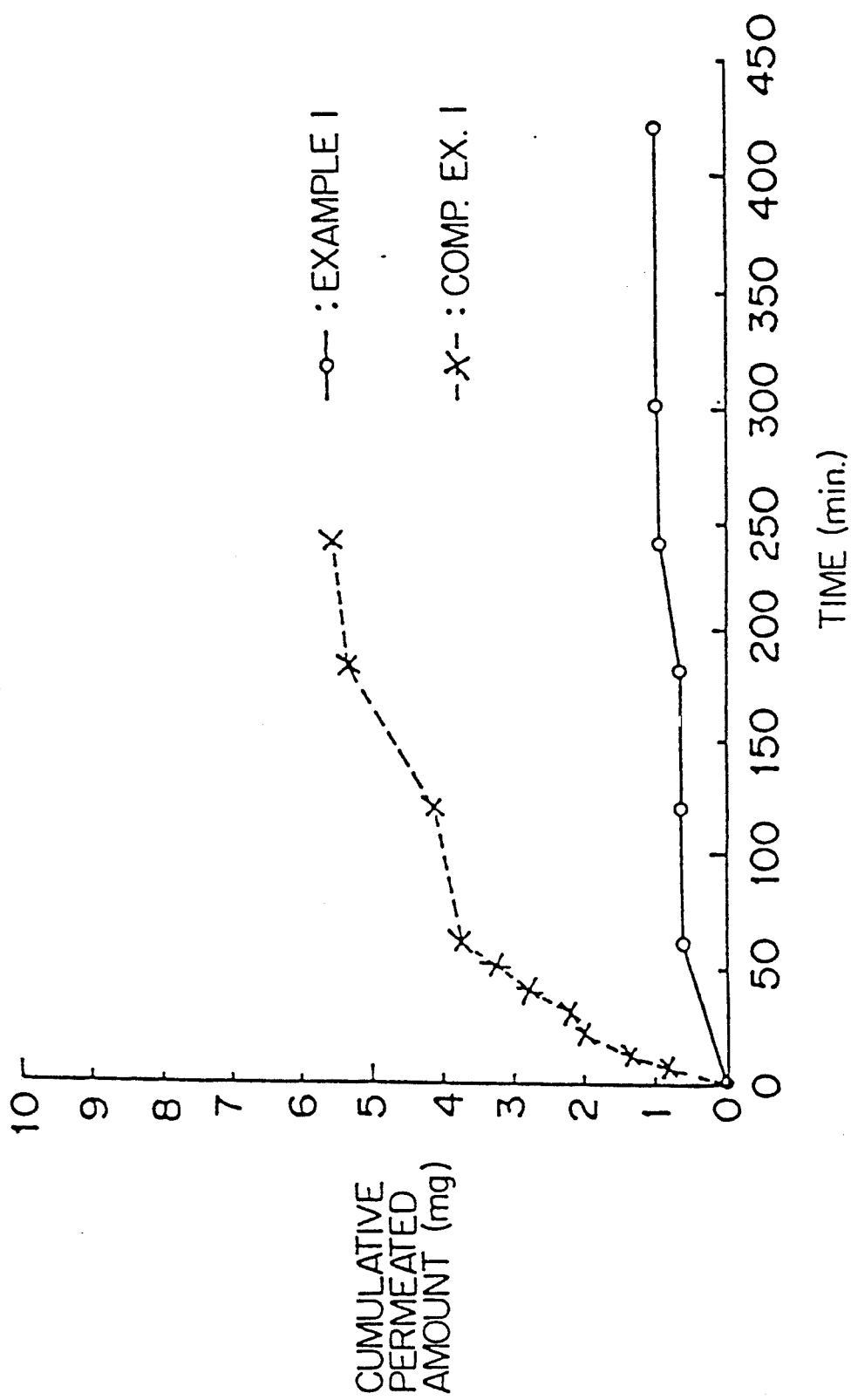
Figure 4:
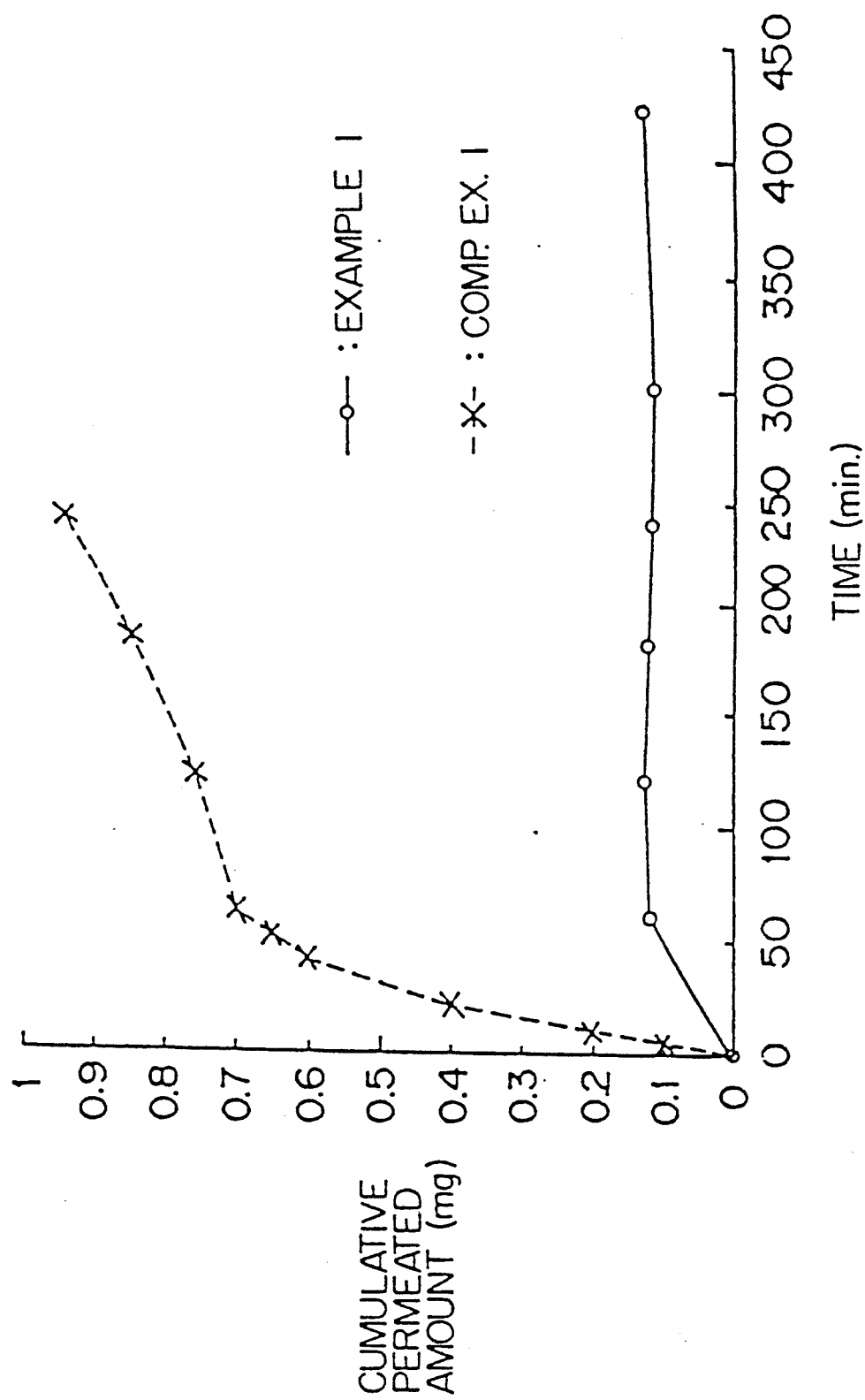
Figure 5:
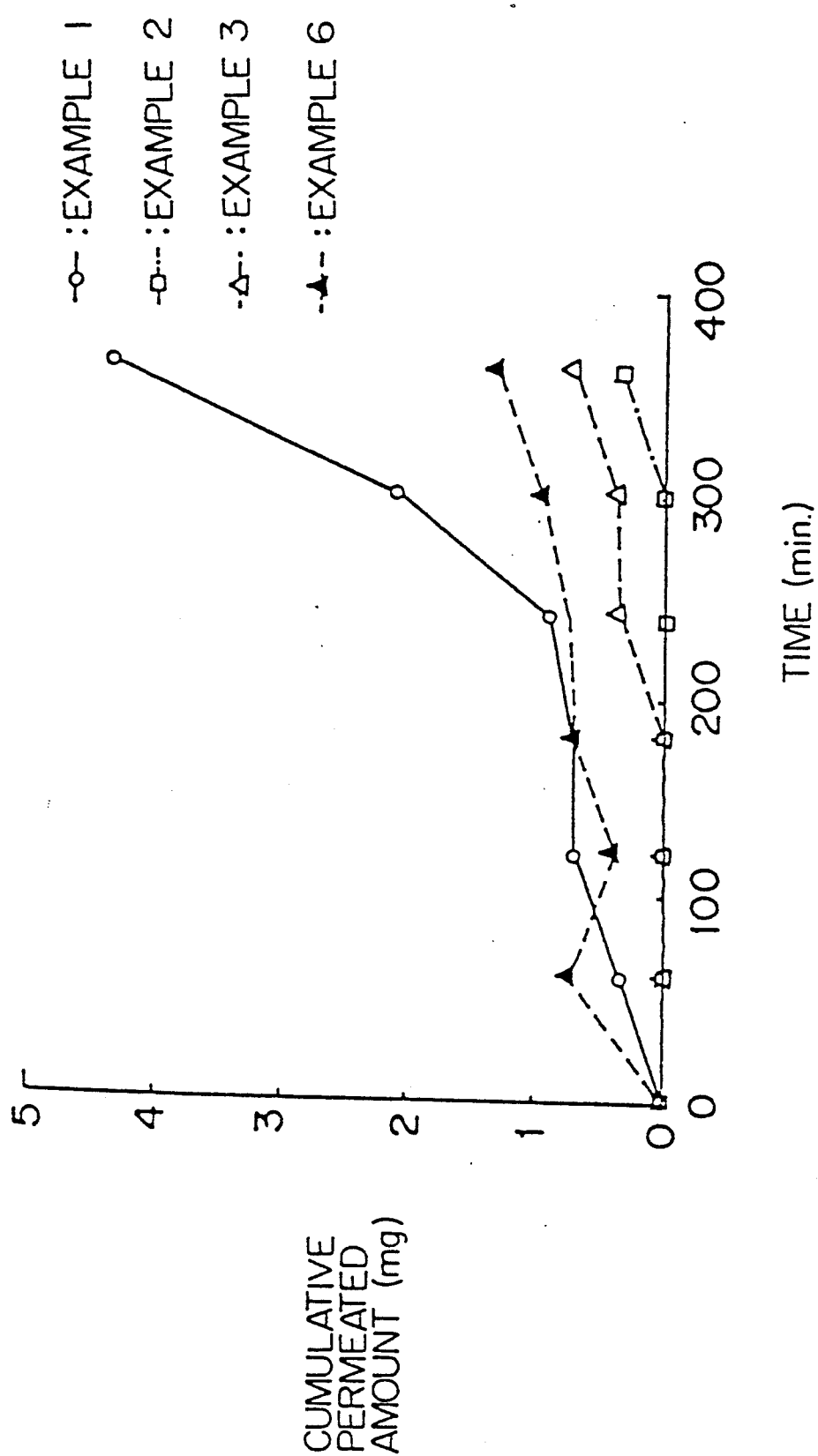
Figure 6:
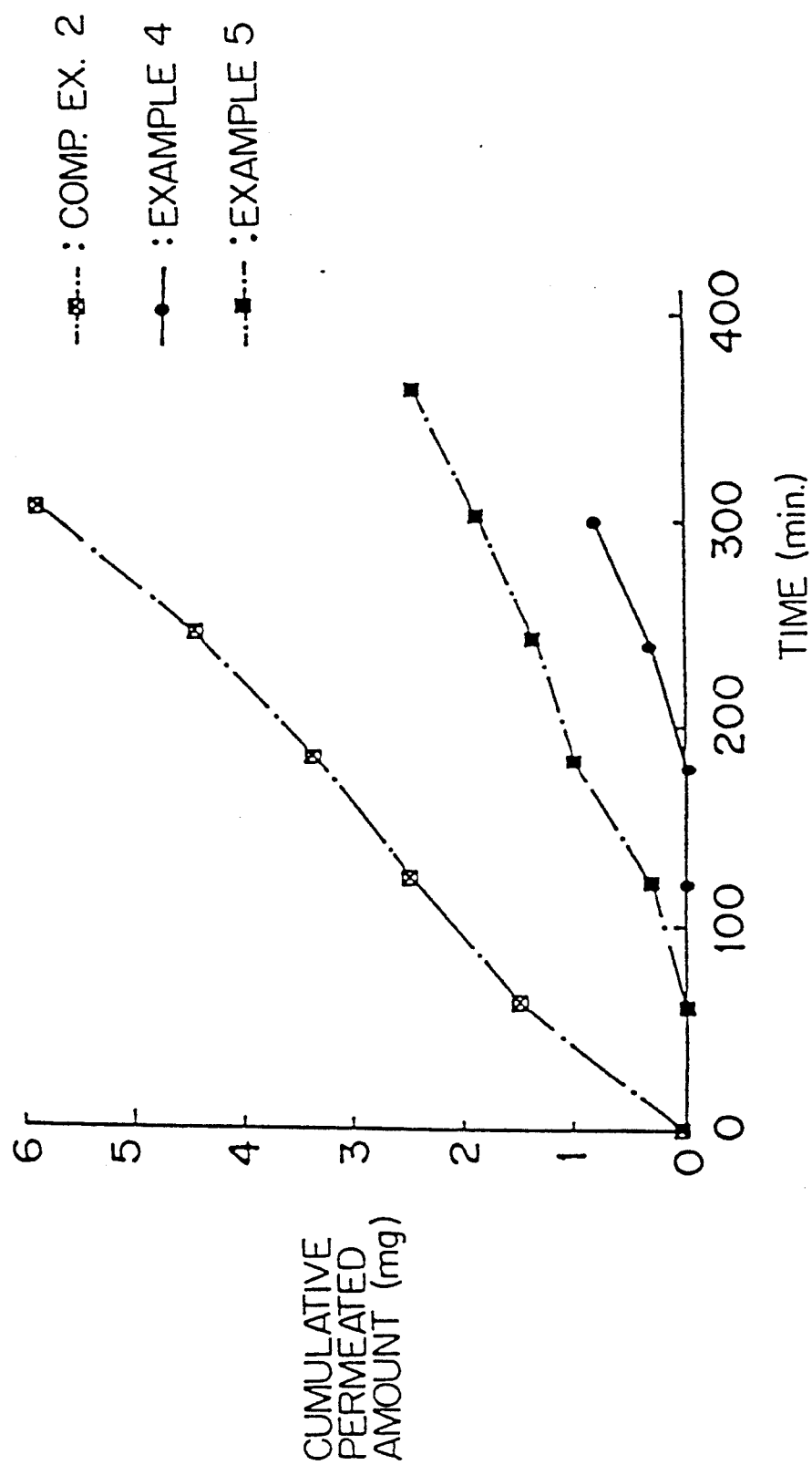

In the formula (I), the radically polymerizable group X includes $CH_2=CH-COO-$, $CH_2=C(CH_3-COO-$,

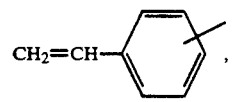

$CH_2=CH-$, $CH_2=CH-OCO-$ and the like. As the group X, a methacryloxy group and an acryloxy group are preferred.

m in the formula (I) is usually a number of 1 to 10, preferably 1 to 6, more preferably 3. When m is larger than 10, the effects of silicone (organopolysiloxane) are deteriorated.

Specific examples of the hydrocarbon or halogenated hydrocarbon group for $R^1$ are a methyl group, an ethyl group, a phenyl group, a trifluoropropyl group and the like. Among them, a methyl group is preferred.

Preferred examples of the Y group for $R^1$ is a group of the formula:

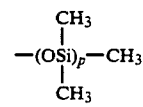

in which p is a number of 5 to 100, preferably 5 to 50.

n is usually a number of 5 to 100, preferably 5 to 50. When the amount of the organopolysiloxane is too small, the copolymer has insufficient functionality, lubricity or water repellency. When said amount is too large, the copolymer tends to lose film forming ability, solubility or adhesivity to other materials.

Specific examples of $R^2$ are a methyl group, an ethyl group, a phenyl group, a trifluoropropyl group and the like. Among them, a methyl group is preferred.

Specific examples of the silicon-containing monomer (A) are

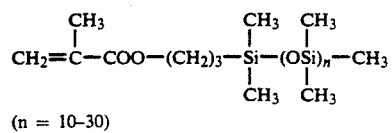

(n = 10-30)

-continued

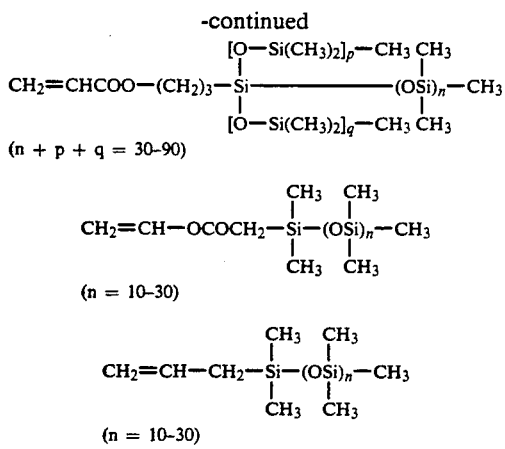

(n + p + q = 30-90)

$$CH_2=CH-OCOCH_2-\underset{\underset{CH_3}{|}}{\overset{\overset{CH_3}{|}}{Si}}-(OSi)_n-CH_3$$
$$\phantom{CH_2=CH-OCOCH_2-Si-(OSi)_n}\underset{CH_3}{|}\phantom{-CH_3}\underset{CH_3}{|}$$

(n = 10-30)

$$CH_2=CH-CH_2-\underset{\underset{CH_3}{|}}{\overset{\overset{CH_3}{|}}{Si}}-(OSi)_n-CH_3$$
$$\phantom{CH_2=CH-CH_2-Si-(OSi)_n}\underset{CH_3}{|}\phantom{-CH_3}\underset{CH_3}{|}$$

(n = 10-30)

The introduction of the compound (A) in the copolymer improves spreading easiness of the composition over the skin and provides good feeling during and after application of the composition.

The amount of the compound (A) in the copolymer is from 1 to 15% by weight, preferably from 1 to 10% by weight, more preferably from 3 to 6% by weight based on the total weight of the components (A), (B), (C) and (D). When the amount of the compound (A) is less than 1% by weight, the formed film has insufficient lubricity. When said amount is larger than 15% by weight, the polymer has decreased effect for preventing permeation of the irritative materials.

Preferred example of the alkyl acrylate (B) is an alkyl acrylate having 1 to 6 carbon atoms in the alkyl group, in particular, ethyl acrylate, propyl acrylate or butyl acrylate. The amount of the alkyl acrylate (B) is from 30 to 70% by weight, preferably from 50 to 65% by weight based on the total weight of the components (A), (B), (C) and (D). When the amount of the alkyl acrylate (B) is less than 30% by weight, the film formed from the copolymer has insufficient flexibility. When said amount is larger than 70% by weight, the film becomes tacky and has insufficient strength.

Preferred example of the alkyl methacrylate (C) is an alkyl methacrylate having 1 to 6 carbon atoms in the alkyl group, in particular, methyl methacrylate or ethyl methacrylate. The amount of the alkyl methacrylate (C) is from 0 to 30% by weight based on the total weight of the components (A), (B), (C) and (D). When this amount is larger than 30% by weight, the formed film is hard.

Since the alkyl acrylate imparts flexibility to the copolymer film and the alkyl methacrylate imparts stiffness to the copolymer film, flexibility and stiffness of the copolymer film can be adjusted by the combination of these two components.

Specific examples of the mono-ethylenically unsaturated monomer having the carboxyl group (D) are acrylic acid, methacrylic acid, crotonic acid, itaconic acid, maleic acid, fumaric acid, half-esters of maleic acid, half-esters of fumaric acid and the like. The monomer (D) improves the adhesivity of the copolymer film to the skin and reduces electrostatic charge. In addition, the monomer (D) imparts swellability with or dispersibility in a weak alkali such as an amine, aqueous ammonia or an aqueous solution of soap to the copolymer and makes it easy to remove the film from the skin. The amount of the monomer (D) is from 5 to 45% by weight, preferably from 10 to 40% by weight, more preferably from 10 to 20% by weight based on the total weight of the components (A), (B), (C) and (D). When the amount of the monomer (D) is less than 5% by weight, it is not easy to remove the copolymer film from the skin. When said amount is larger than 45% by weight, the water repellency and water resistance of the copolymer are deteriorated and the copolymer film becomes harder.

The silicone-acrylic copolymer of the present invention may further comprise other monomer in addition to the above essential components. Examples of the other monomer are vinyl monomers such as vinyl acetate, 2-hydroxyethyl methacrylate and N-vinylpyrrolidone. The amount of the other monomer is preferably not larger than 20% by weight based on the total weight of the components (A), (B), (C) and (D). Otherwise, the copolymer may no achieve the effects of the present invention.

The silicone-acrylic copolymer has a weight average molecular weight of 50,000 to 1,300,000, preferably 100,000 to 800,000 measured by the GPC method.

The silicone-acrylic copolymer of the present invention may be prepared by copolymerizing the above monomers by a per se conventional method. The polymerization mode may be solution polymerization, emulsion polymerization or suspension polymerization.

For example, the solution polymerization is carried out by heating the monomer mixture in a solvent in the presence of a polymerization initiator while stirring. Examples of the solvent are methanol, ethanol, isopropanol, acetone, methyl ethyl ketone, methyl acetate, ethyl acetate, ethyleneglycol monoalkyl ether and the like. Examples of the polymerization initiator are solvent-soluble ones such as dibenzoyl peroxide, cumene hydroperoxide, diisopropyl peroxydicarbonate and azobisisobutyronitrile.

The emulsion polymerization is carried out by heating a dispersion of an emulsifier, a water-soluble polymerization initiator and the monomer mixture in water while stirring. Preferred examples of the emulsifier are anionic or nonionic surfactants such as sodium laurylsulfate, sodium lauroylsarcosine, polyoxyethylene lauryl ether, polyoxyethylenesorbitan monooleate, sorbitan sesquioleate, glycerin monostearate, aliphatic acid esters with sucrose and the like. Examples of the water-soluble polymerization initiator are ammonium persulfate, potassium persulfate, hydrogen peroxide, tert.-butyl hydroperoxide and the like. Optionally, a reducing agent such as sodium hydrogensulfite and L-ascorbic acid can be used.

The solution or emulsion of the copolymer obtained from the polymerization process may be used as the skin-protecting composition of the present invention. Preferably, to the solution of the copolymer, water, ethylene glycol or a hydrocarbon base non-solvent (e.g. n-hexane) is added to precipitate the copolymer from the solution. Then, the precipitated copolymer is washed with water or the non-solvent, purified and dried. The emulsion of the copolymers coagulated with the addition of an acid or an aqueous solution of a salt such as sodium sulfate and calcium chloride and the coagulated copolymer is washed with water, purified and dried. From the suspension of the copolymer, the copolymer is recovered, washed with water, purified and dried. Then, to the copolymer, a suitable medium is added to prepare the skin-protecting composition of the present invention.

The skin-protecting composition of the present invention comprises the copolymer and a medium and can be in the form of a solution, a cream or a spraying liquid. The medium is preferably a solvent such as a lower alcohol or a solvent which is generally used in the preparation of a loiton, a cream or a spraying liquid. Preferred examples of the medium are ethanol, isopropanol and a mixture of water and ethanol or isopropanol.

Preferably, the skin-protecting composition of the present invention is in the solution form. The concentration of the copolymer in the solution is from 1 to 30% by weight, preferably from 5 to 10% by weight. When the mixed solvent of water and an alcohol is used, a ratio of water to the alcohol can vary in a wide range.

To the skin-protecting composition of the present invention, other resin may be added. For example, the addition of a cellulose derivative such as ethylcellulose or hydroxypropylcellulose will improve the film properties of the copolymer.

The film of the copolymer is not or hardly contaminated with edible oil, oil mist, foods (e.g. ketchup, sauce, soy sauce, etc.), ink, crayon, marker ink and the like, or if contaminated, the contamination can be easily removed. The film of the copolymer is easily removed with a weakly alkaline water or ethanol.

The film of the copolymer of the present invention effectively prevents permeation of irritative materials such as perillaldehyde, benzyl alcohol, sodium benzoate, benzalkonium chloride, chlorohexidine gluconate, and the like.

When a small amount of the skin-protecting composition is applied to the skin, a very thin film of the copolymer is formed on the skin. The formed film has sufficient water resistance and acid resistance, is not contaminated, has good elongation and flexibility, and well adheres to the skin without malaise. In addition, the copolymer is very safe to the skin since it has no or little irritation to the skin and well blocks the irritative materials.

The formed film can be easily and safely removed from the skin with a weakly alkaline aqueous solution such as an aqueous solution of soap or an alcohol such as ethanol.

PREFERRED EMBODIMENTS OF THE INVENTION

The present invention will be illustrated by following Examples, in which "parts" are by weight unless otherwise indicated.

Example 1

A copolymer having the following monomeric composition was prepared by solution polymerization in ethyl acetate by using diisopropyl peroxydicarbonate. Namely, in a closed reactor equipped with a stirrer which had been replaced with nitrogen gas, ethyl acetate (75 parts) was charged, and an internal temperature of the reactor was adjusted at 55° C. To the content of the reactor, diisopropyl peroxydicarbonate (1.0 part) was added. Then, the following monomer mixture

| Monomer | parts |
|---|---|
| (1) The silicon-containing monomer A | 10 |
| (2) Methyl methacrylate (MMA) | 15 |
| (3) Ethyl acrylate (EA) | 60 |
| (4) Methacrylic acid (MAA) | 15 | and 0.5% solution of diisopropyl peroxydicarbonate in ethyl acetate (100 parts) were added over 4 hours while keeping the internal temperature of the reactor at 55° C. The content of the reactor was stirred at 55° C. for 2 hours and at 77° C. for 3 hours to complete polymerization, followed by cooling to room temperature.

In a mixer, the reaction mixture was poured. To the mixture, n-hexane (1000 parts) was gradually added while stirring under shear to precipitate the copolymer, which was recovered by filtration, washed with n-hexane and dried. Yield of the copolymer was 94%. The copolymer had the weight average molecular weight of $12.2 \times 10^4$ (by GPC).

The copolymer was dissolved in ethanol at a concentration of 30% to obtain a transparent solution.

Examples 2–6

In the same manner as in Example 1 but using a monomer mixture shown in Table 1, a copolymer was prepared, and a 30% solution of the copolymer in ethanol was obtained. The monomeric composition and the weight average molecular weight of the copolymer are shown in Table 1.

Example 7

In the same manner as in Example 1 but using a mixed solvent of ethanol and water in a weight ratio of 70:30 in place of ethanol, a 30% solution of the copolymer in the mixed solvent was obtained.

Example 8

In the same manner as in Example 1 but using 3 parts of the silicon-containing monomer A, 25 parts of methyl methacrylate, 57 parts of butyl acrylate and 15 parts of acrylic acid, a 30% solution of the copolymer in ethanol was obtained.

Comparative Examples 1 and 2

In the same manner as in Example 1 but using a monomer mixture shown in Table 1, a 30% solution of the copolymer in ethanol was obtained. The monomeric composition and the weight average molecular weight of the copolymer are shown in Table 1.

TABLE 1

| Example No. | Monomeric composition (% by weight) | | | | Molecular weight ($\times 10^4$) |
|---|---|---|---|---|---|
| | Si-cont. monomer | MMA | EA | MAA | |
| 1 | A, 10.0 | 15.0 | 60.0 | 15.0 | 12.2 |
| 2 | A, 3.0 | 18.5 | 63.5 | 15.0 | 8.8 |
| 3 | A, 6.0 | 17.0 | 62.0 | 15.0 | 12.2 |
| 4 | B, 6.0 | 17.0 | 62.0 | 15.0 | 9.9 |
| 5 | A, 10.0 | 15.0 | 55.0 | 20.0 | 16.5 |
| 6 | A, 6.0 | 0 | 62.0 | 32.0 | 32.1 |
| Comp. 1 *1) | 0 | 0 | 85.0 | 15.0 | 80.0 |
| Comp. 2 | A, 30.0 | 5.0 | 50.0 | 15.0 | 27.2 |

Note: *1) Ethylcellulose was added in an amount of 20% by weight based on the weight of the copolymer.

The silicon-containing monomers A and B are as follows:

(1) Silicon-containing monomer A

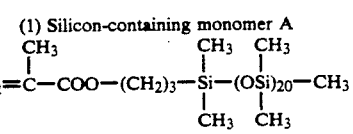

(2) Silicon-containing monomer B

-continued

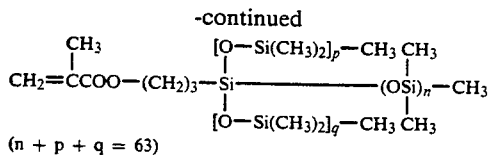

(n + p + q = 63)

Experiments

With each of the solutions prepared in Examples 1-6 and Comparative Examples 1 and 2, the following tests were carried out:

1. Film permeability

With a table coater (HIRONO KINZOKU CO., LTD.), a film of about 50 μm in thickness was formed from the solution. With the formed film, effect for preventing permeation of a chemical was evaluated in vitro.

In a Franz type cell having a permeation area of 10 cm², the film was attached with using a 0.45 μm membrane filter as a support. After filling purified water in a receptor part, a 1% aqueous solution of the chemical to be tested (1 ml) was charged in a donor cell. Then, an amount of the chemical which was permeated to the receptor cell through the film was measured as time passes and a cumulative permeated amount of the chemical was calculated. As model compounds for irritative materials having different molecular weights, benzyl alcohol, sodium benzoate, benzalkonium chloride and chlorohexidine gluconate were used.

The cumulative permeated amounts of the chemicals are plotted in FIGS. 1 to 6.

The films formed from the copolymer of Examples 1 to 6 had much better effects for preventing permeation of the chemicals than the films formed from the copolymer of Comparative Examples 1 and 2.

Figure 7:
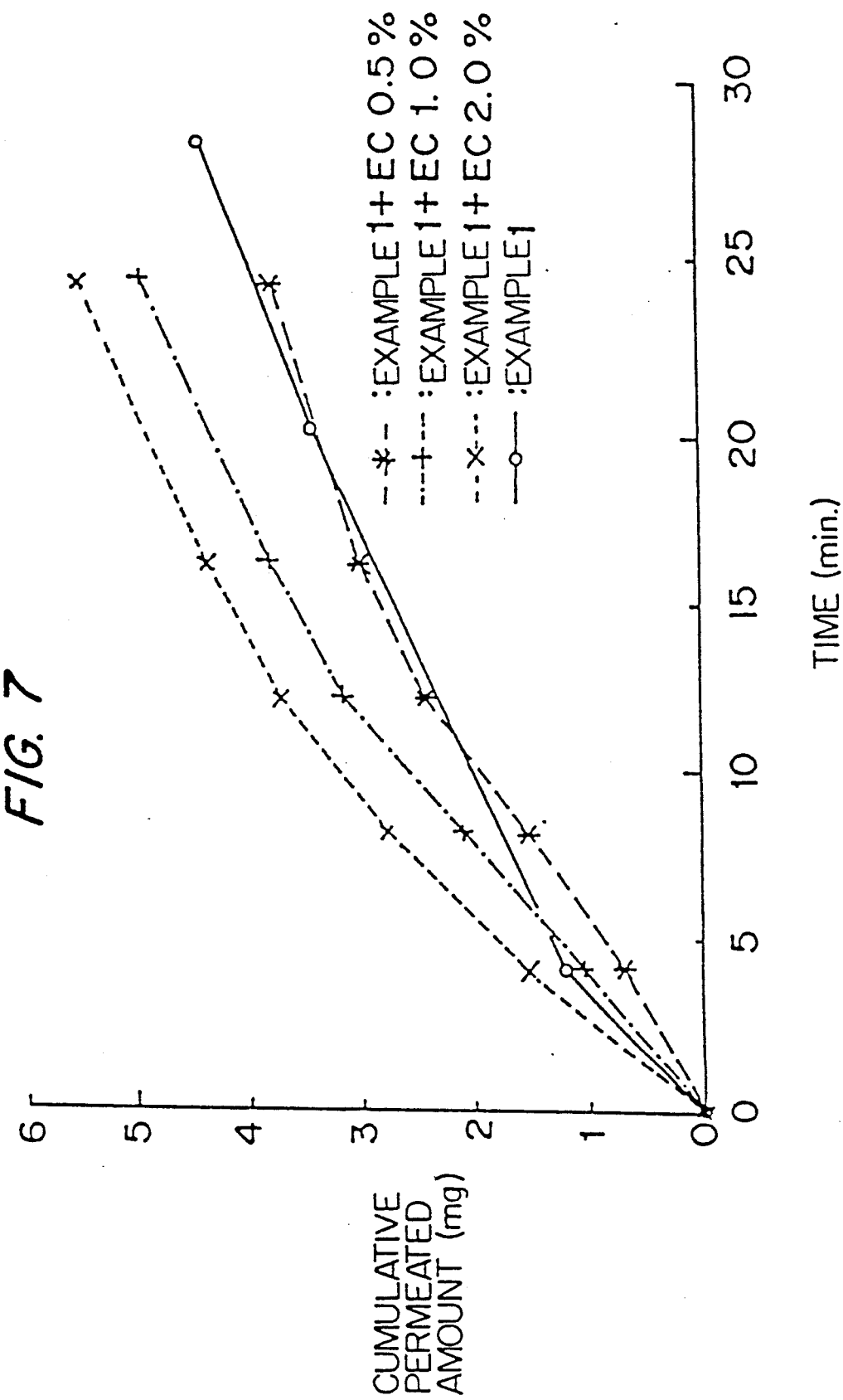
Figure 8:
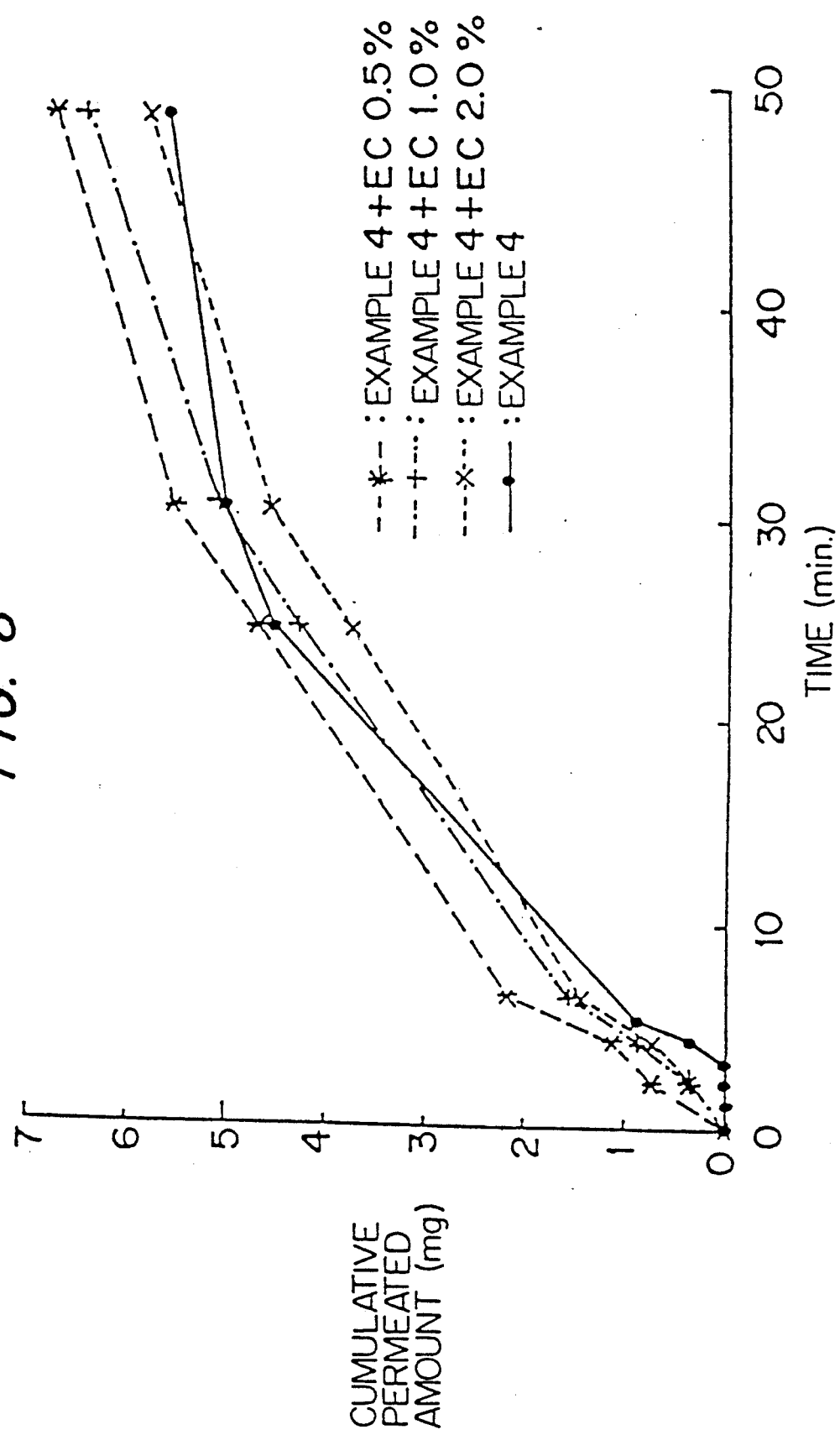

From the solution prepared in Example 1 or 4 to which ethylcellulose (EC) was added in an amount of 0.5, 1.0 or 2.0% by weight, a film was formed, and effect for preventing permeation of benzyl alcohol was evaluated. The results of cumulative permeated amounts are plotted in FIGS. 7 and 8. The addition of ethylcellulose does not decrease the effect for preventing permeation of the chemicals.

2. Film formability

On a clean film of polyethylene terephthalate (PET), a solution was coated with a doctor knife to a solid amount of 5 g/m² and dried at room temperature. All the solutions formed transparent dense films with lubricity and gloss but no tackiness.

3. Brushing resistance

On the film formed on the PET film, a No. 3 abrasive piece was reciprocated 50 times under load of 200 g. Then, the surface condition of the film was observed. No irregularity was observed.

4. Removal of formed film

On the film formed on the PET film, a quantity of 2% aqueous ammonia or ethanol was dropped and easiness of film removal was observed.

All the films were swelled and peeled with aqueous ammonia after 2 minutes from dropping and completely removed with a cloth. All the films were dissolved in ethanol after 2 minutes from dropping and completely removed with a cloth.

The properties of the films formed from the solutions of Examples 2, 3 and 1 are summarized in Table 2.

TABLE 2

| | Example No. | | |
|---|---|---|---|
| | 2 | 3 | 1 |
| Appearance | Transparent | Transparent | Transparent |
| Lubricity | Slightly | Yes | Yes |
| Contact angle with water (°) | 95 | 99 | 100 |
| Elongation (%) | 171 | 157 | 167 |
| Tensile strength (g/mm²) | 510 | 600 | 570 |
| Dissolution time (min.) | | | |
| in water (pH = 8) | 10–20 | 10–20 | 20–30 |
| in water (pH = 10) | <5 | <5 | <5 |
| in ethanol | Dissolved | Dissolved | Dissolved |

What is claimed is:

1. A skin-protecting composition which comprises an uncrosslinked silicone-acrylic copolymer which comprises (A) 1 to 15% by weight of a silicon-containing monomer of the formula:

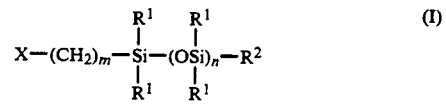

wherein X is a radically polymerizable group; $R^1$ groups are the same or different and each a $C_1$–$C_{20}$ hydrocarbon or halogenated hydrocarbon group or a group Y of the formula:

in which $R^3$ groups are the same or different and each a $C_1$–$C_{20}$ hydrocarbon or halogenated hydrocarbon group, p is a number of 5 to 100, provided that the number of the Y group among the $R^1$ groups is 0, 1 or 2; $R^2$ is a $C_1$–$C_{20}$ hydrocarbon or halogenated hydrocarbon group; m is a number of 1 to 10; and n is a number of 5 to 100, (B) 30 to 70% by weight of an alkyl acrylate, (C) 0 to 30% by weight of an alkyl methacrylate, and (D) 5 to 45% by weight of a mono-ethylenically unsaturated monomer having a carboxyl group, and a medium.

2. The skin-protecting composition according to claim 1, wherein the silicon-containing compound (A) is selected from the group consisting of

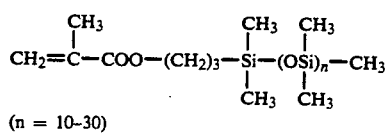

(n = 10–30)

-continued

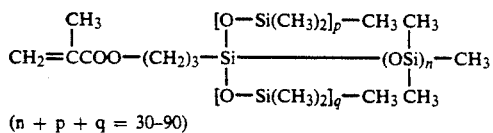

(n + p + q = 30-90)

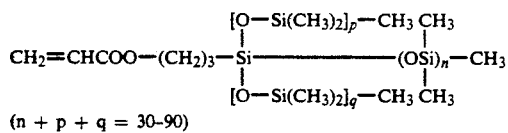

(n + p + q = 30-90)

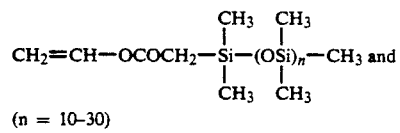

(n = 10-30)

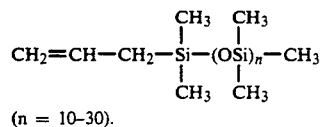

(n = 10-30).

3. The skin-protecting composition according to claim 1, wherein the alkyl acrylate (B) is selected from the group consisting of ethyl acrylate, propyl acrylate and butyl acrylate.

4. The skin-protecting composition according to claim 1, wherein the alkyl methacrylate (C) is selected from the group consisting of methyl methacrylate and ethyl methacrylate.

5. The skin-protecting composition according to claim 1, wherein the mono-ethylenically unsaturated monomer (D) is selected from the group consisting of acrylic acid, methacrylic acid, crotonic acid, itaconic acid, maleic acid, fumaric acid, half-esters of maleic acid and half-esters of fumaric acid.

6. The skin-protecting composition according to claim 1, wherein the silicone-acrylic copolymer has a weight average molecular weight of 50,000 to 1,300,000.

7. The skin-protecting composition according to claim 1, wherein the medium is selected from the group consisting of ethanol, isopropanol, a mixture of water and ethanol and a mixture of water and isopropanol.

8. The skin-protecting composition according to claim 1, which is a solution of the copolymer in the medium.

9. The skin-protecting composition according to claim 8, wherein a concentration of the copolymer in the medium is from 1 to 30% by weight.

10. The skin-protecting composition according to claim 1, which further comprises a cellulose derivative selected from the group consisting of ethylcellulose and hydroxypropylcellulose.

* * * * *

UNITED STATES PATENT AND TRADEMARK OFFICE
CERTIFICATE OF CORRECTION

PATENT NO.  : 5,229,435
DATED       : July 20, 1993
INVENTOR(S) : Yoshio SASAKI et al.

It is certified that error appears in the above-identified patent and that said Letters Patent is hereby corrected as shown below:

Cover page, lefthand column, next to "[75] Inventors:", please change "Sakai" to --Sasaki--.

Signed and Sealed this

Fifth Day of April, 1994

Attest:

BRUCE LEHMAN

Attesting Officer

Commissioner of Patents and Trademarks